United States Patent [19]

Martin et al.

[11] 4,299,983

[45] Nov. 10, 1981

[54] CHEMICAL PROCESS

[75] Inventors: Trevor I. Martin, Burlington; John M. Lennon, Mississauga, both of Canada

[73] Assignee: Xerox Corporation, Stamford, Conn.

[21] Appl. No.: 81,309

[22] Filed: Oct. 3, 1979

[51] Int. Cl.$^3$ ............................................. C07C 85/02
[52] U.S. Cl. ..................................... 564/394; 564/433; 564/434
[58] Field of Search ................. 260/576; 564/394, 433, 564/434

[56] References Cited

U.S. PATENT DOCUMENTS

| | | | |
|---|---|---|---|
| 1,882,759 | 10/1932 | Britton et al. | 260/576 |
| 1,980,102 | 11/1934 | Semon | 260/576 X |
| 2,052,633 | 9/1936 | Kranz | 260/576 X |
| 2,064,797 | 12/1936 | Holsten | 260/576 X |
| 2,165,747 | 7/1939 | Cook | 260/576 |
| 2,799,705 | 7/1957 | De Pree et al. | 260/577 X |

FOREIGN PATENT DOCUMENTS 1496639 12/1977 United Kingdom ................ 260/576

OTHER PUBLICATIONS

Nagai, "Chemical Abstracts", vol. 69, Ab. No. 106301p (1968).
Nara, "Chemical Abstracts", vol. 82, Ab. No. 111692q (1975).
Nara et al., "Journal of the Japanese Chemical Society", vol. 9, pp. 1, 499-1, 501 (1976).

*Primary Examiner*—John Doll

[57] ABSTRACT

A process for the production of symmetrical and unsymmetrical substituted diarylamines is disclosed. The process provides said diarylamines in high yield and purity by the reaction of a salt of an arylsulfonic acid and an alkali metal salt of a primary arylamine in the presence of an inorganic alkali metal salt.

16 Claims, 2 Drawing Figures

CHEMICAL PROCESS

This invention relates to the production of amines and in particular to the production of symmetrical and unsymmetrical diarylamines.

Many compounds in the class of diarylamines have been used in the past as intermediates in dye synthesis. More recently, substituted arylamines have found extensive use as polymer stabilizers, in particular as antioxidants for rubbers and elastomers. Also, substituted diphenylamines have recently been employed as additives for lubricating oils, particularly as corrosion inhibitors. Certain alkyl and alkyloxydiphenylamines have exhibited antibacterial activities superior to penicillin and streptomycin for specfic bacterial strains.

Unsymmetrical alkyl substituted diarylamines have been difficult to prepare in high yield as the reactions employed in the past have a low efficiency of conversion and are multistep processes. Many of the better methods for preparation of unsymmetrical alkyldiphenylamines consist of condensation of a phenol with an aniline in the presence of an acid or Lewis acid catalyst. The product of such process invariably contains homologs of the desired diphenylamine due to the self condensation of the aniline under acidic conditions.

Recently, 3-methyldiphenylamine has been produced by the amination of m-toluene sulfonate with sodium anilide in aniline solution as disclosed in Nippon Kagakukai, Nippon Kagaka Kaishi 9, 1499 (1976). Although this process provides an unsymmetrical substituted diphenylamine, it is not economically feasible since m-toluene sulfonic acid is not commercially available and is difficult to prepare. Diarylamines have been prepared from alkali metal salts of aromatic sulfonic acids and alkali metal anilides according to British Pat. No. 1,496,639. Secondary aromatic amines such as N-aryl naphthylamines and N,N'-diaryl naphthalenediamine are formed by the treatment of a naphthyl sulfonic acid salt or naphthyl disulfonic acid salt with the sodium salts of primary aromatic amines in the presence of excess aromatic amine.

Satisfactory yields of diarylamines are obtained in the prior art but at the expense of relatively high temperatures over an extended reaction time and in some cases under high pressure.

Thus, there is needed a process for conveniently and efficiently producing unsymmetrical and symmetrical substituted diarylamines utilizing low temperatures, short reaction times and precursors which are readily available in high quantity and low cost.

SUMMARY OF THE INVENTION

It is the object of this invention to provide an economically efficient process for the production of substituted diarylamines of high purity from readily available precursors utilizing the minimum number of process steps.

In accordance with this invention, there is provided a process for preparing a compound represented by the formula

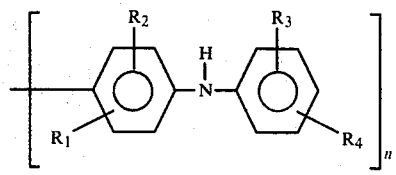

wherein n is an integer selected from 1, and 2, $R_1$, $R_2$, $R_3$ and $R_4$ are radicals independently selected from the group consisting of hydrogen, alkyl having from 1 to about 20 carbon atoms, phenyl and alkaryl radicals, and no more than three of $R_1$, $R_2$, $R_3$ and $R_4$ is hydrogen, by the reaction of a substituted or unsubstituted alkali metal salt of a primary arylamine with a substituted or unsubstituted arylsulfonic acid salt in a reaction medium containing an inorganic alkali metal salt. Normally the salt of the primary aromatic amine is formed in situ by the addition to the reaction vessel of the primary arylamine and an appropriate amount of an alkali metal or alkali metal hydride or an alkali metal amide.

The salt of the primary aryl amine is allowed to react with the salt of the arylsulfonic acid in the presence of an appropriate amount of an inorganic alkali metal salt. The substituted diarylamine is thus provided in high yield and exceptional purity in a reaction of short duration by reacting the above-mentioned materials at elevated temperatures in the range of from about 150° C. to about 400° C.

In the preferred embodiment of this invention, the arylsulfonic acid is added to the reaction vessel already containing an excess of the primary arylamine salt and an inorganic alkali metal salt wherein the acid is converted in situ to its alkali metal salt. Preferably the inorganic alkali metal salt is added to the reaction vessel before the addition of the sulfonic acid but such order of addition is not critical.

The product is separated by quenching the reaction mixture with water or dilute acid to convert the alkali metal salt of the diarylamine into the free amine and to provide an aqueous and organic phase separation. The organic phase is then subjected to fractional distillation under reduced pressure to recover the solvent as the free amine and the product, diarylamine, at temperatures in the range of from about 70° C. to about 250° C.

There is thus provided a convenient process for the production of diarylamines which produces generally in excess of 90 percent yield of the desired amine based upon the initial quantity of sulfonic acid, said amine having a purity in excess of 99 percent.

The diarylamine produced by the process of this invention is free of isomers or homologs. As will be more fully discussed below, the rate of conversion of arylsulfonic acid salt to diarylamine is greater in the presence of an inorganic alkali metal salt than in the absence of the inorganic alkali metal salt for the same reaction temperature.

DETAILED DESCRIPTION OF THE INVENTION

Typical arylsulfonic acid salts useful in the process of this invention are represented by the formula

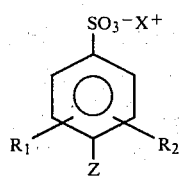

wherein X is an alkali metal, $R_1$ and $R_2$ are radicals independently selected from the group consisting of hydrogen, alkyl having from 1 to about 20 carbon atoms, phenyl, alkaryl and Z is hydrogen or a para substituted phenyl sulfonic acid alkali metal salt.

The other reactant in the process of this invention comprises an alkali metal salt of a primary arylamine. The alkali metal utilized to form the salt of the arylamine may be the same or different than the alkali metal salt of the acid referred to above. Also, the salt may be formed in the reaction vessel utilized to perform the reaction of this invention. For example, the primary arylamine may be placed in a reaction vessel and treated with an alkali metal, alkali metal amide or hydride to form the salt. Typical arylamine salts useful in the process of this invention may be represented by the structure

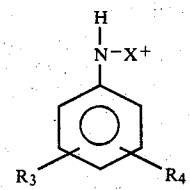

wherein X is an alkali metal, $R_3$ and $R_4$ are radicals independently selected from the group consisting of hydrogen, alkyl having from 1 to about 20 carbon atoms, phenyl and alkaryl.

Most amine salts can be prepared by the reaction of the corresponding arylamine with the alkali metal, its hydride or amide. It is preferred that the amide be utilized since it is easier to handle than the alternative materials.

An inorganic alkali metal ion is added to the reaction mixture in the form of a salt. Potassium chloride is preferred because of its availability and its effect on reactivity. A clear demonstration of this effect is graphically illustrated in FIG. 1 as will be more fully described below. The presence of the inorganic alkali metal halide has been found to greatly increase the rate of conversion of the acid salt to the diarylamine. Also, the kind of alkali metal has an additional effect in that one metal ion creates a faster reaction than another. With respect to the members of the alkali metal family, an increase in rate of reaction has been observed in the order $Li < Na < K < Cs$.

It is preferred that the above-described reactants be combined in a reaction vessel together with a suitable reaction medium. Typical solvents include xylene, dimethylacetamide or, preferably, the corresponding primary arylamine, the salt of which is utilized as one of the reactants in the process. In the event of utilizing a primary arylamine reaction medium, the amount of amine actually added to the reactor must be increased to provide the quantity required for the reaction medium in excess of that taken up as the alkali metal salt. Generally, the molar ratio of the reactants is in the range of about 2 moles of the primary arylamine salt to 1 mole of the acid salt. However, in the event the free acid is added to the reaction vessel for the purpose of forming the salt in situ, about 3 moles of primary arylamine salt to 1 mole of the free acid is utilized. Generally, the mole ratio of the added inorganic alkali metal salt to the alkali metal salt of the primary arylamine is in the range of 0.1:1 to 2:1. Generally, the amount of solvent is in the range of 40 to 50 percent, by weight, of the total reaction mixture.

To further illustrate the process of this invention, the following reactions demonstrate the formation of the reactive salts of the primary arylamine and arylsulfonic acid:

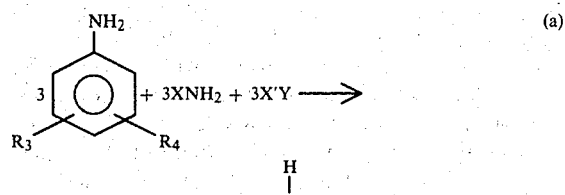

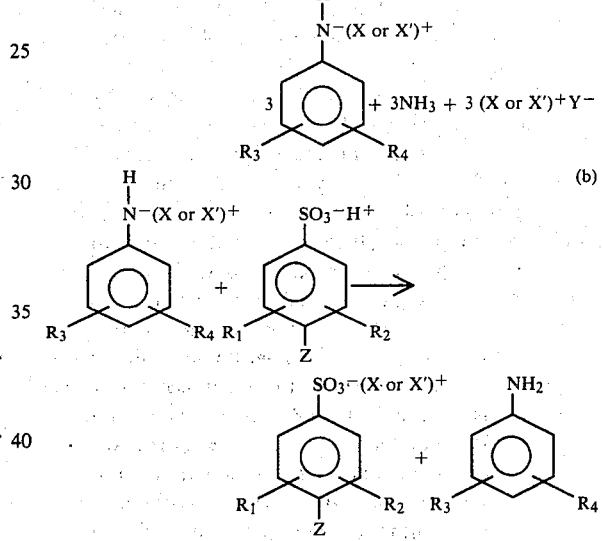

wherein $R_1$, $R_2$, $R_3$ and $R_4$, X and Z are as defined above, Y is an inorganic anion and X' is an alkali metal.

The reactions (a) and (b) above are simplified in accordance with this invention by utilizing an ordered addition of reactants as described above. In accordance with the process of this invention, the following reactions occur:

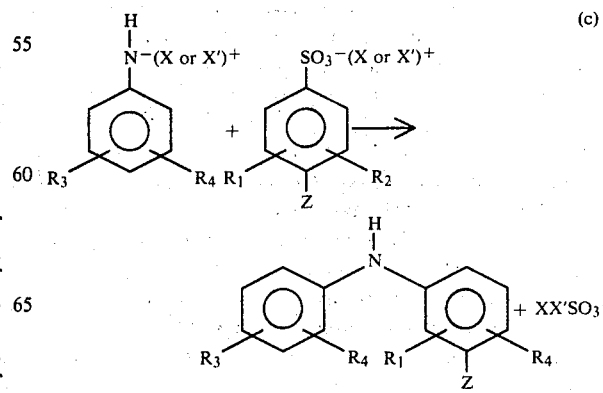

-continued

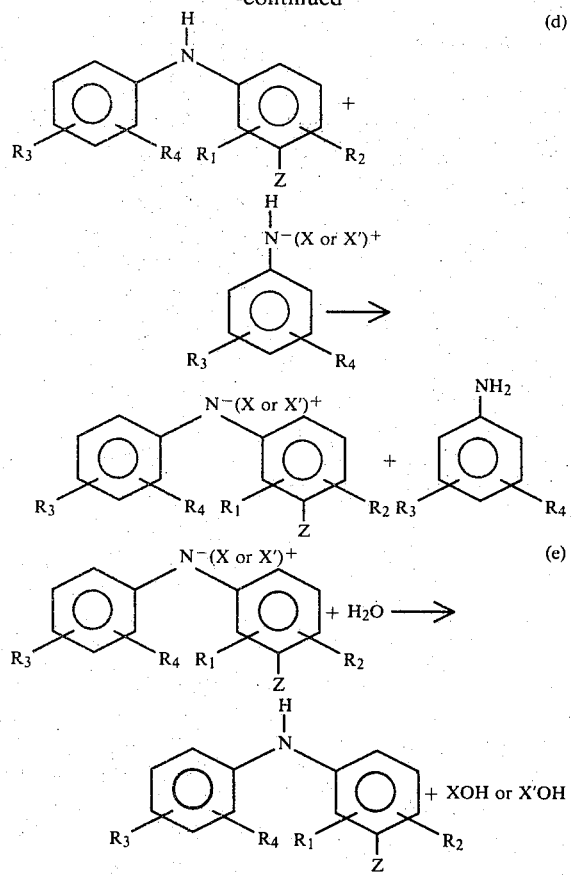

wherein $R_1$, $R_2$, $R_3$, $R_4$, X, X' and Z are as described above provided each X and X' is independently selected and Y is an inorganic anion radical.

The sodium salt of the primary arylamine is most economically employed. When utilizing the sodium salt of the primary arylamine, the reaction time has been found to be greatly shortened by adding a potassium halide. Alternatively, the arylacid salt may be preformed and added to the reaction mixture together with the primary arylamine, the amine salt and the inorganic alkali metal salt.

The hydrolysis of the diarylamine salt as described in equation (e) conveniently provides a separation of the reaction mixture into an aqueous phase and an organic phase. As is noted in reactions (c) and (e) above, the undesired side products are insoluble in the organic phase. The desired diarylamine is easily separated from the primary arylamine by distillation.

One of the ordinary skill can easily envision a cyclic process wherein the primary arylamine is employed as the solvent and recycled upon recovery from the reaction mixture.

From the above reactions, one notes that the desired diarylamine is easily separated from the inorganic portion of the reactants and then easily distilled from the other organic materials in the mixture.

As mentioned above, $R_1$, $R_2$, $R_3$ and $R_4$, substituents on the phenyl radicals, are independently selected from the group of various radicals. Alkyl radicals include preferably methyl but can also include the ethyl, propyl, n-butyl, t-butyl, pentyl, hexyl, heptyl, octyl, nonyl, decyl, undecyl, dodecyl and other alkyl radicals having up to about 20 carbon atoms. Alkaryl radicals include, for example, methylphenyl, ethylphenyl and methylethylphenyl.

Inorganic alkali metal salts added to the reaction mixture to increase the reaction rate include various salts of sodium, potassium, cesium and rubidium. Typical anions useful in the process of this invention include chloride, fluoride, bromide, iodide, sulfates and phosphates. Because of their economical availability, the chloride salts are preferred.

Among the advantages of the process of this invention are high yields generally in excess of 90 percent of the desired diarylamine. This product is obtained in this high yield in a single step process although illustrated above by several reactions. As will be more fully described in the examples below, these reactions can conveniently take place in the same reactor in quick succession and a portion of the reaction product can be recycled for use. Also, a very high purity product is obtained completely uncontaminated with other unsubstituted and substituted diarylamines. The problem with self condensation of primary arylamines in prior art methods for producing diarylamines has thus been overcome. Further, the process is relatively inexpensive by utilizing readily available technical grade raw materials and no catalyst of any kind. Since all of the materials are ecologically easily disposed of, the process presents major advantages over prior art methods wherein catalysts are employed.

As will be further illustrated below in the examples, the process of this invention generally utilizes relatively low temperatures in the range of from about 150° to about 220° C., preferably in the range of from about 160° to about 200° C. and is therefore conserving of energy and apparatus structure. Many different symmmetrical and unsymmetrical, substituted diarylamines are produced in accordance with the process of this invention by varying the substitution on the aryl structure.

The above-described advantages and others will become apparent upon reading the following specific examples wherein parts and percentages are by weight unless otherwise stated. The following examples are not intended to limit the invention in any way and are utilized to illustrate the process of this invention.

BRIEF DESCRIPTION OF THE DRAWINGS

The attached drawings further illustrate the process of this invention wherein.

A description of the processes of each of the above-mentioned reactions are described in the following examples.

DESCRIPTION OF THE PREFERRED EMBODIMENTS

EXAMPLE I

In this example, there is described two procedures which were conducted for purposes of comparison. Two substantially isothermal reactions are described which, while serving the purpose of comparison, do not represent the practical, economical embodiments of either procedure. The first described procedure below is representative of the prior art while the second procedure is in accordance with the process of this invention.

Into a reactor fitted with a reflux condenser, thermometer, mechanical stirrer and gas inlet tube were charged sodium amide (47.7 parts or 1.222 mole) and m-toluidine (400 parts or 3.738 mole). The reaction was stirred at 60° C. to liberate ammonia after which the temperature was raised to 180° C. The reactor is purged with nitrogen over the course of the reaction. Dry, preformed sodium benzenesulfonate (100 parts or 0.555 mole) was added rapidly while the temperature is maintained at 180° C.±1° C. with stirring for a period of 7½ hours to achieve maximum conversion of benzenesulfonate to 3-methyldiphenylamine. The amine is recovered by hydrolysis and distillation to provide a 90 percent yield of 3-methyldiphenylamine having a melting point of 27°–27.5° C. after recrystallization from hexane at 0° C.

As a comparable reaction to that described above, there is charged into a suitably equipped reactor sodium amide (47.7 parts or 1.222 mole), potassium chloride (136.7 parts or 1.833 mole), and m-toluidine (400 parts or 3.738 mole). This mixture was stirred at 60° C. to liberate ammonia. The temperature of the reaction mixture was then raised to 180° C. with constant stirring and the maintenance of nitrogen purge in the reactor. Dry, preformed sodium benzenesulfonate (100 parts or 0.555 mole) was added rapidly and the temperature maintained at 180° C.±1° C. for a period of 3 hours during which time substantially all of the benzenesulfonate is converted to 3-methyldiphenylamine. Upon hydrolysis, separation and distillation, there was obtained 3-methyldiphenylamine in a yield of 91 percent having a melting point of 27°–27.5° C. when recrystallized as described above.

Figure 1:
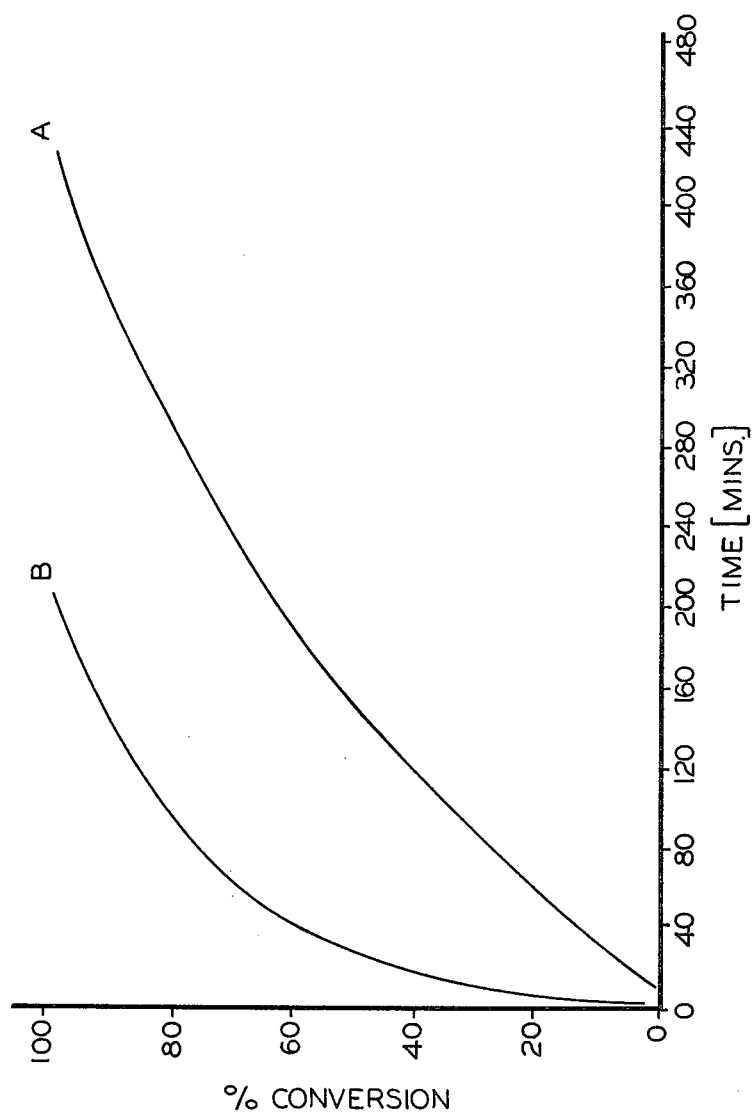
FIG. 1 is a graphical representation of comparable rates of reaction for producing an unsymmetrical, substituted diphenylamine under isothermal conditions to indicate the effect of added inorganic alkali metal salt to the reaction mixture.

During each of the procedures above described, samples of the reaction mixture were taken and analyzed to determine the conversion of benzenesulfonate to 3-methyldiphenylamine. In FIG. 1, there is graphically displayed the percent conversion versus the time of reaction wherein curve A represents the data obtained by the procedure in accordance with the prior art and curve B represents the data obtained in the procedure in accordance with this invention.

EXAMPLE II

Figure 2:
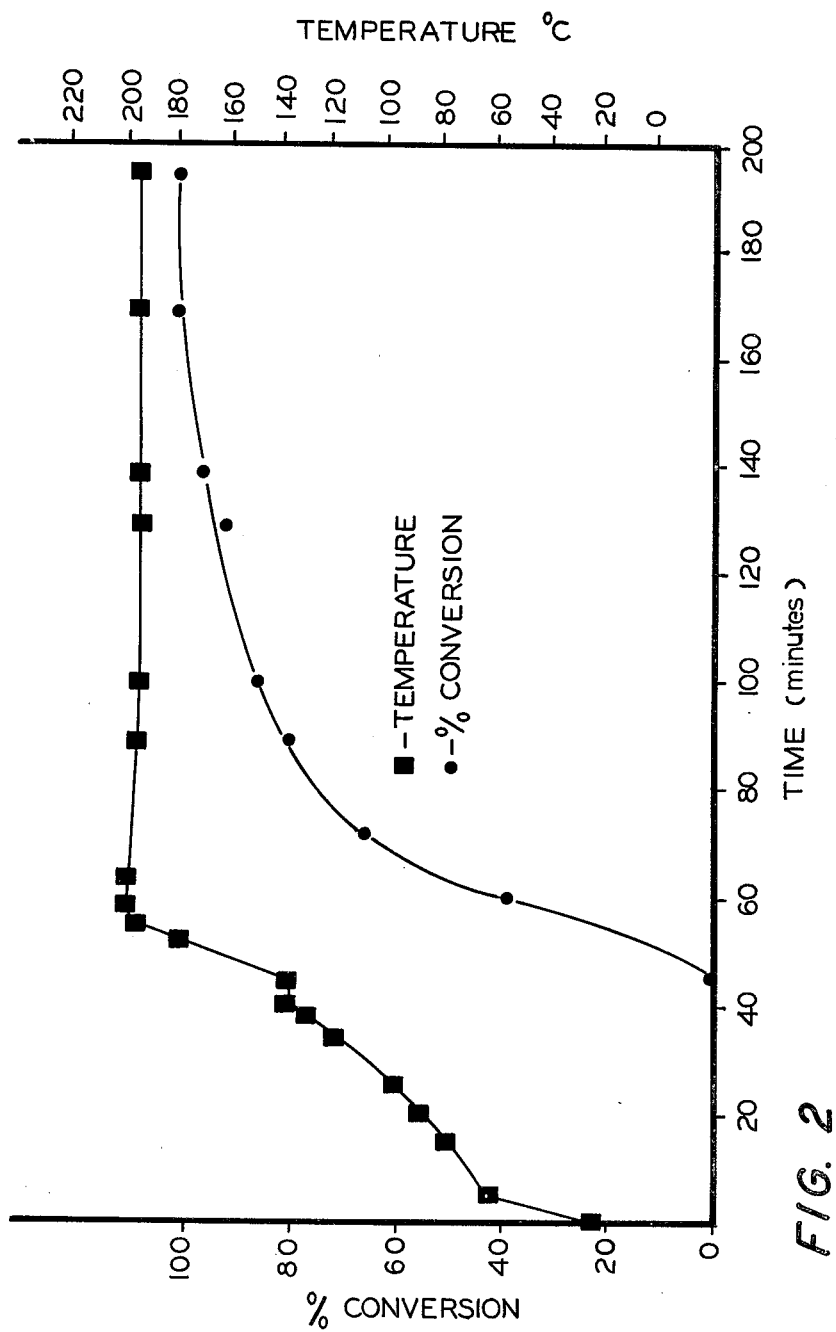
FIG. 2 is a graphical representation of the rate of reaction for producing an unsymmetrical substituted diphenylamine in accordance with a preferred method of this invention.

Into a suitable reactor there is added under inert atmosphere about 800 parts of potassium chloride, 415 parts of sodium amide and about 1,870 parts of m-toluidine. The temperature of the reaction mixture immediately rises to about 65° C. with evolution of ammonia. The reaction mixture is then heated rapidly to about 140° C. at which time the external heating is discontinued and the atmosphere is again purged with an inert gas. Approximately 548 parts of 90 percent benzenesulfonic acid maintained at 70° C. is slowly added to the hot reaction mixture over a period of about 15 minutes. During the addition of the acid, the temperature rises to approximately 200° C. and then subsides to approximately 195° C. After the addition of the acid, the temperature is controlled by added heat at about 195° C.±1° C. The reaction is continued during the next 2½ hours during which time samples of the reaction mixture are taken and analyzed for 3-methyldiphenylamine. The data obtained is graphically represented in FIG. 2. When the amount of m-toluidine reaches 26 percent, the reaction is considered complete with respect to the conversion of benzenesulfonic acid to the diphenylamine. At the end of the reaction, the reaction mixture is cooled to 50° C. and quenched with 2 liters of water containing concentrated sulfuric acid (155 parts). The mixture is agitated for about 30 minutes to allow hydrolysis to proceed and to form two separate layers. The organic phase is transferred to a distillation apparatus. Under reduced pressure m-toluidine is recovered at a temperature range of 70° C. to 115° C. and 3-methyldiphenylamine is recovered at a temperature range of 125° C. to 185° C. The overall yield of 3-methyldiphenylamine is 99 percent (based upon pure benzenesulfonic acid) having a purity of 99.7 percent.

EXAMPLE III

To a suitably equipped reaction vessel were charged 141 parts of m-toluidine and 49 parts of dry potassium chloride. The resultant suspension was treated with 26 parts of metallic potassium under a nitrogen purge at 60° C. to form potassium m-toluidide. The reaction mixture, with stirring was brought to a temperature of 140° C. 4,4'-biphenyldisulfonic acid (31.4 parts) was added over a 15 minute period after which the temperature of the reaction mixture increased to 205° C. After 24 hours of stirring at this temperature, the reaction mixture was quenched into water. The organic layer was separated and distilled under reduced pressure to remove m-toluidine leaving a dark crystalline mass of crude N,N'-bis(3''-methylphenyl)-[1,1'-biphenyl]-4,4'-diamine. The product was purified by chromotography on silica using 20 percent dichloromethane in heptane as an eluant to give 32.8 parts pure N,N'-bis(3''-methylphenyl)-[1,1'-biphenyl]-4,4'-diamine with a melting point of 156.5°–158° C. in 90 percent yield based upon 4,4'-biphenyldisulfonic acid.

EXAMPLE IV

Into a suitably equipped reactor were charged 27.8 parts of sodium amide, 53 parts of potassium chloride and 176 parts of 3,5-dimethylaniline. The stirred reaction mixture was heated to 140° C. as ammonia was liberated and expelled from the reactor by means of a nitrogen purge. With continued stirring, 37.8 parts of 90 percent benzenesulfonic acid was added to the reactor as the reaction mixture was heated to 180° C. for 3.5 hours. The reaction mixture was then quenched with water producing two separate layers. The organic layer containing 3,5-dimethylaniline and 3,5-dimethyldiphenylamine was subjected to distillation under reduced pressure to give 31.8 parts of crude 3,5-dimethyldiphenylamine at the fraction taken between 105° to 115° C. at 0.1 mm. of Hg. After two recrystallizations from hexane, there was obtained 29.6 parts of pure 3,5-dimethyldiphenylamine representing a yield of 70 percent of said product having a melting point of 51°–52° C.

EXAMPLE V

The procedure of Example IV is repeated with the exception that 3,4-dimethylaniline was substituted for 3,5-dimethylaniline. After a reaction time of 3.5 hours, the crude reaction product was recrystallized once from hexane to give an 84 percent yield of 3,4-dimethyldiphenylamine having a melting point of 55°–55.5° C.

EXAMPLE VI

Into a suitably equipped reactor were charged 19.1 parts of sodium amide, 36.4 parts potassium chloride and 149 parts of 4-n-butylaniline. After evolution of an ammonia and with stirring, the mixture was heated to 140° C. and treated with 27.8 parts of 90 percent of benzenesulfonic acid. The reaction was allowed to proceed with stirring at 185° C. for 16 hours. After quenching with water and separation of the two phases, 20.4 parts of 4-n-butyldiphenylamine was obtained as a colorless oil distilling at 140°–142° C. at 0.2 mm. of Hg.

Into a suitably equipped reactor were charged 43 parts of sodium amide, 82 parts of potassium chloride and 237.8 parts of m-toluidine. Ammonia was evolved and purged with nitrogen while heating the reaction mixture with stirring to a temperature of 140° C. at which temperature 108.7 parts of 4-dodecyl benzenesulfonic acid was added to the reaction mixture. The reaction mixture was maintained at 20° C. for a period of 21 hours with constant stirring after which the mixture was quenched into water and the organic layer separated. Distillation of the organic layer under reduced pressure removed m-toluidine and as a second fraction, 3-methyl-4'-dodecyl diphenylamine as a pale yellow oil having a boiling range of 133°–155° C. at 0.60 mm. of Hg. in a yield of 90 percent.

What is claimed is:

1. The process for preparing a compound represented by the formula

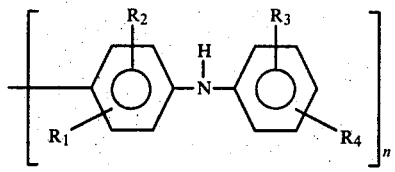

wherein n is an integer of 1 or 2, $R_1$, $R_2$, $R_3$ and $R_4$ are radicals independently selected from the group consisting of hydrogen, alkyl having from 1 to about 20 carbon atoms, phenyl, and alkaryl which comprises reacting an arylsulfonic acid alkali metal salt represented by the formula

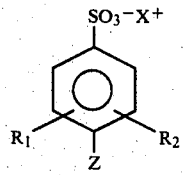

wherein X is an alkali metal, $R_1$ and $R_2$ are as defined above, and Z is hydrogen or a para substituted phenyl sulfonic acid alkali metal salt; with an alkali metal salt of an arylamine represented by the formula

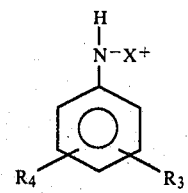

wherein X, $R_3$ and $R_4$ are as defined above, in the presence of an added inorganic alkali metal salt in a suitable reaction medium.

2. The process of claim 1 wherein the arylsulfonic acid salt is an alkali metal salt of benzenesulfonic acid.

3. The process of claim 1 wherein the amine salt is an alkyl substituted arylamine.

4. The process of claim 3 wherein the amine salt is an alkali metal m-toluidide.

5. The process of claim 1 wherein the reaction is carried out at a temperature in the range of from about 160° C. to about 200° C.

6. The process of claim 3 wherein the alkyl substituent has from 1 to 4 carbon atoms.

7. The process of claim 1 wherein the alkali metal of the amine salt is sodium and wherein the added inorganic alkali metal salt is a potassium salt.

8. The process of claim 7 wherein the sulfonic acid salt is a sodium salt and wherein the added inorganic alkali metal salt is a potassium salt.

9. The process of claim 1 wherein the arylamine metal salt is provided in the reaction vessel by the addition of a primary arylamine and an alkali metal amide.

10. The process of claim 9 wherein the alkali metal amide is sodium amide.

11. The process of claim 10 wherein said primary arylamine is m-toluidine.

12. The process of claim 1 wherein the arylsulfonic acid salt is a salt of 4,4'-biphenyldisulfonic acid.

13. The process of claim 1 wherein the mole ratio of inorganic alkali metal salt to the alkali metal salt of the primary arylamine is in the range of from about 0.1 to 1 to about 2 to 1.

14. The process of claim 1 wherein the arylsulfonic acid salt is formed in situ by the addition of the corresponding arylsulfonic acid to the reaction medium containing excess primary arylamine salt and wherein the arylamine salt is added to the reaction medium prior to said acid.

15. A process for preparing 3-methyldiphenylamine which comprises reacting the alkali metal salt of m-toluidine with an alkali metal salt of benzene sulfonic acid in excess m-toluidine in the presence of an added inorganic alkali metal salt.

16. The process of claim 15 wherein the alkali metal salt of m-toluidine is formed in situ by the addition of sodium amide and the inorganic alkali metal salt is a potassium salt.

* * * * *